(12) United States Patent
He et al.

(10) Patent No.: US 10,314,708 B2
(45) Date of Patent: Jun. 11, 2019

(54) ADAPTIVELY POSITIONED MITRAL VALVE CLOSURE PLATE BLOCKER FOR REPAIRING MITRAL REGURGITATION

(71) Applicant: Jiangsu University, Zhenjiang (CN)

(72) Inventors: Zhaoming He, Zhenjiang (CN); Kailiang Zhang, Lubbock, TX (US); Teng Jing, Zhenjiang (CN)

(73) Assignee: Jiangsu University, Zhenjiang (CN)

( * ) Notice: Subject to any disclaimer, the term of this patent is extended or adjusted under 35 U.S.C. 154(b) by 121 days.

(21) Appl. No.: 15/322,577

(22) PCT Filed: Jul. 9, 2014

(86) PCT No.: PCT/CN2014/081897
§ 371 (c)(1),
(2) Date: Dec. 28, 2016

(87) PCT Pub. No.: WO2016/000274
PCT Pub. Date: Jan. 7, 2016

(65) Prior Publication Data
US 2017/0151057 A1    Jun. 1, 2017

(30) Foreign Application Priority Data

Jun. 30, 2014    (CN) .......................... 2014 1 0311083

(51) Int. Cl.
*A61F 2/24*    (2006.01)
(52) U.S. Cl.
CPC ............ *A61F 2/246* (2013.01); *A61F 2/2445* (2013.01); *A61F 2250/0006* (2013.01)
(58) Field of Classification Search
CPC ........ A61F 2/24; A61F 2/2442; A61F 2/2445; A61F 2/2448; A61F 2/246; A61F 2/2451
See application file for complete search history.

(56) References Cited

U.S. PATENT DOCUMENTS

| 6,869,444 B2 * | 3/2005 | Gabbay ................. A61F 2/2445 128/898 |
| 7,704,277 B2 | 4/2010 | Zakay et al. |

(Continued)

FOREIGN PATENT DOCUMENTS

| CN | 101056596 A | 10/2007 |
| CN | 103517688 A1 | 1/2014 |
| WO | 2006086434 A1 | 8/2006 |

OTHER PUBLICATIONS

International Search Report re PCT/CN2014/081897, dated Feb. 27, 2015, 6 pgs.

*Primary Examiner* — Seema Mathew
(74) *Attorney, Agent, or Firm* — Greenberg Traurig, LLP

(57) ABSTRACT

An adaptively positioned mitral valve closure plate blocker for repairing mitral regurgitation, comprising a suture and shaping ring (4.1) sutured on a mitral ring (2.1) and a closure plate (4.2); the closing plate (4.2) comprises a tongue-shaped plate and a strut (4.3) located at the top of the tongue-shaped plate and connected to the suture and shaping ring; the closing plate (4.2) can be connected to the suture and shaping ring (4.1), being capable of flapping back and forth and twisting left and right. The suture and shaping ring is sutured on the valve ring (2.1) of the mitral valve (2) of a patient in a thoracotomy and open heart surgery, thus shaping the disease expanded mitral ring (2.1), and supporting the closing plate (4.2); when a heart contracts and valve leaflets close, the closing plate (4.2) flaps and twists depending on the position of a regurgitation opening at the free edge of the valve leaflets to realize adaptive positioning of the closing plate (4.2), so that the closing plate (4.2) is at the free edge when two valve leaflets are closed, covering the regurgitation opening, and is tightly attached to the free edge of the valve leaflets, reducing or avoiding regurgitation of the mitral valve (2).

4 Claims, 13 Drawing Sheets

(56) References Cited

U.S. PATENT DOCUMENTS

| | | | | |
|---|---|---|---|---|
| 9,005,279 B2* | 4/2015 | Gabbay | ................ | A61F 2/2454 |
| | | | | 623/2.36 |
| 2005/0038508 A1* | 2/2005 | Gabbay | ................ | A61F 2/2445 |
| | | | | 623/2.36 |
| 2006/0229708 A1* | 10/2006 | Powell | ............ | A61B 17/00234 |
| | | | | 623/1.24 |
| 2010/0262233 A1* | 10/2010 | He | ................ | A61F 2/2445 |
| | | | | 623/2.36 |
| 2013/0325115 A1 | 12/2013 | Maisano et al. | | |
| 2014/0039615 A1* | 2/2014 | Padala | .................. | A61F 2/2454 |
| | | | | 623/2.37 |
| 2014/0350662 A1* | 11/2014 | Vaturi | .................. | A61F 2/2412 |
| | | | | 623/2.1 |
| 2016/0008130 A1* | 1/2016 | Hasin | .................... | A61F 2/2418 |
| | | | | 623/2.37 |
| 2016/0030175 A1* | 2/2016 | Madjarov | ............ | A61F 2/2445 |
| | | | | 623/2.37 |
| 2017/0095332 A1* | 4/2017 | Bruchman | .............. | A61L 27/14 |
| 2018/0214270 A1* | 8/2018 | Subramanian | .......... | A61B 17/00 |

* cited by examiner

ADAPTIVELY POSITIONED MITRAL VALVE CLOSURE PLATE BLOCKER FOR REPAIRING MITRAL REGURGITATION

CROSS REFERENCE TO RELATED APPLICATION

The present application is a 371 U.S. National Stage of International Application No. PCT/CN2014/081897, filed Jul. 9, 2014, which claims the benefit of the earlier filing date of Chinese Patent Application No. 201410311083.6 filed on Jun. 30, 2014, which are each incorporated herein by reference in their entirety.

FIELD OF THE DISCLOSURE

The invention is related to a medical device. More specifically, the invention is related to a mitral valve repair device with novel adaptive location, a mitral valve coaptation plate occluder for repairing mitral regurgitation.

BACKGROUND OF RELATED ART

Reference is first made to FIG. 1, a schematic of a human heart and its four heart valves. Mitral valve 2 lies between the left atrium 1 and the left ventricle 5 to control blood flow unidirectional from the left atrium 1 into the left ventricle 5. A dysfunctional mitral valve does not close properly and leads to regurgitation where blood flows backward from the left ventricle 5 to left atrium 1 during systole. Mitral regurgitation can cause pulmonary congestion and a dilated left ventricle which can ultimately result in heart failure and mortalities.

The mitral valve 2 structure is shown in FIG. 2. Mitral valve is a complex load bearing structure that consists of annulus 2.1, anterior leaflet 2.2, posterior leaflet 2.3, chords 2.4, papillary muscle 3, and the underlying left ventricular myocardium. The anterior 2.2 and posterior leaflets 2.3 are attached to the annulus 2.1. The annulus 2.1 is an anatomical structure joining the leaflets and the left ventricle wall. It is divided into the fibrous annulus in the anteromedial section and the myocardium annulus in the posterolateral section, according to annulus 2.1 histology. The chords originate from the papillary muscles 3 and insert into the leaflets. They prevent the leaflets from prolapsing into the left atrium during systole. The papillary muscles 3 are attached to the wall of the left ventricle.

The normal closure of mitral valve is shown in FIGS. 4 and 3, there is no gap between the anterior and posterior leaflets without regurgitation. When the closure of mitral valve is shown in FIGS. 5 and 6, there is a gap between the anterior and posterior leaflets, and the blood flows back from the left ventricle to the left atrium through the gap in systole, thus the backward flow phenomenon is called mitral regurgitation At present, the common mitral valve repair techniques include triangular or quadrangular resection, slide annuloplasty, ring annuloplasty, chordal cutting and transposition, artificial chord use and, recently, percutaneous technologies. The success of this therapy depends on an understanding of the delicate force balance between the leaflets with lower reliability, resulting to 50% of the mitral regurgitation recurrence in 5 years after the treatment.

SUMMARY

The aim of this invention is to provide a mitral valve coaptation plate occluder of self-adjustable positioning for repairing mitral regurgitation to treat the functional mitral regurgitation disease. The coaptation plate can realize self-adjustable positioning according to the regurgitation gap location of the free edges of the mitral leaflets. The coaptation plate blocks the regurgitation gap and coaptates the free edge of the mitral leaflets to reduce or prevent regurgitation during systole. This simple design has a good reliability.

In order to achieve the above purpose, the invention adopts the following technical proposal:

The mitral valve coaptation plate occluder of self-adjustable positioning for repairing mitral regurgitation, which includes the annuloplasty ring sutured on the mitral annulus, and coaptation plate. The coaptation plate is comprised of a tongue plate and a supporting rod at the top of the tongue plate connecting the annuloplasty ring. The coaptation plate connecting on the annuloplasty ring can swing and roll.

Preferably, the outer surface of the annuloplasty ring is wrapped with a fabric material.

Preferably, the surface of coaptation plate, the supporting rod and the annuloplasty ring are wrapped with a layer of blood compatible material.

Preferably, the blood compatible material is polyurethane and/or pericardial membrane.

Preferably, the coaptation plate is made of rigid material. The tongue plate must have the same arc with coaptation line of the free edges of the anterior and posterior leaflets of the mitral valve.

Preferably, the tongue plate is made of flexible material, and the flexible tongue plate has embeddied elastic metal or polymer materials frame. The flexible tongue plate can achieve swinging and rolling with a curve shape under the pressure caused by the anterior and posterior leaflets of the mitral valve.

Preferably, there is a hinge between the supporting rod and annuloplasty ring.

Preferably, the tongue plate and supporting rod work as one part. The two curved cylinders are located at the both ends of the supporting rod, and they are perpendicular to the supporting rod. The cylinder and the annuloplastyr ring have the same arc. There are two cylindrical cavities or the oblong holes in the annuloplasty ring. The cylindrical cavities are parallel with the annuloplasty ring at the connection position of the supporting rod. The oblong hole connected external cylindrical cavity. The diameter and length of the cylindrical cavity are larger than the cylinder. The supporting rod is inserted into the oblong hole. The two ends of the supporting rod are inserted into the cylindrical cavity.

Preferably, there are triangular holes at the top of the tongue plate. Three vertices of the triangular-like holes are rounded. The support rod is inserted into a triangular hole. The contact part of the support rod and the tongue plate is oblong, and its transverse length is less than the longitudinal length in the cross section. The two ends of the support rod are cylindrical, The annuloplasty ring has two oblong holes, and its transverse length is greater than the longitudinal length. The two ends of the supporting rod are inserted into the oblong holes.

Preferably, three vertices of the triangular holes are rounded.

Preferably, there is a rigid connection between the supporting rod and annuloplasty ring.

Preferably, the height of the supporting rod is above the plane of the suture ring.

The invention provides a device of the mitral valve coaptation plate occluder of self-adjustable positioning for repairing mitral regurgitation. The coaptation plate can achieve self-adjustable positioning by means of swing and rolling within a range of angle. The annuloplasty ring can be sutured on the patient's mitral annulus by the open heart surgery. The annuloplasty ring plays a role of correcting the dilated mitral annulus and supporting the coaptation plate. When the heart valve is closed, the coaptation plate will swing or roll according to the regurgitant gap location of the free edges of the mitral leaflets to realize self-adjustable positioning. The coaptation plate blocks the regurgitant gap and touch the free edge of the mitral leaflets to reduce or prevent regurgitation during systole.

Figure 1:
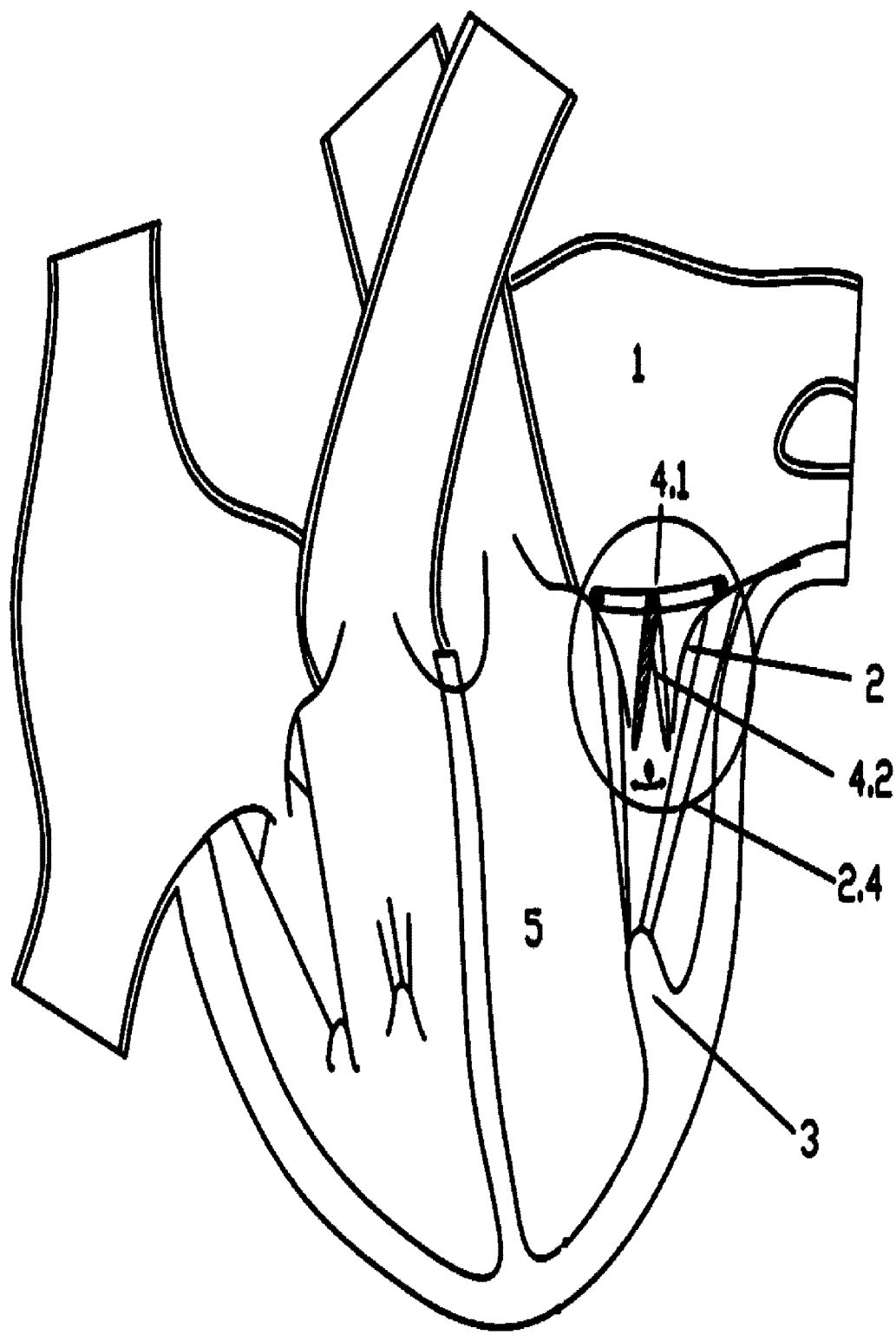
FIG. 1 is a depiction of the location of the mitral valve coaptation plate occluder of self-adjustable positioning for repairing mitral regurgitation.
Figure 2:
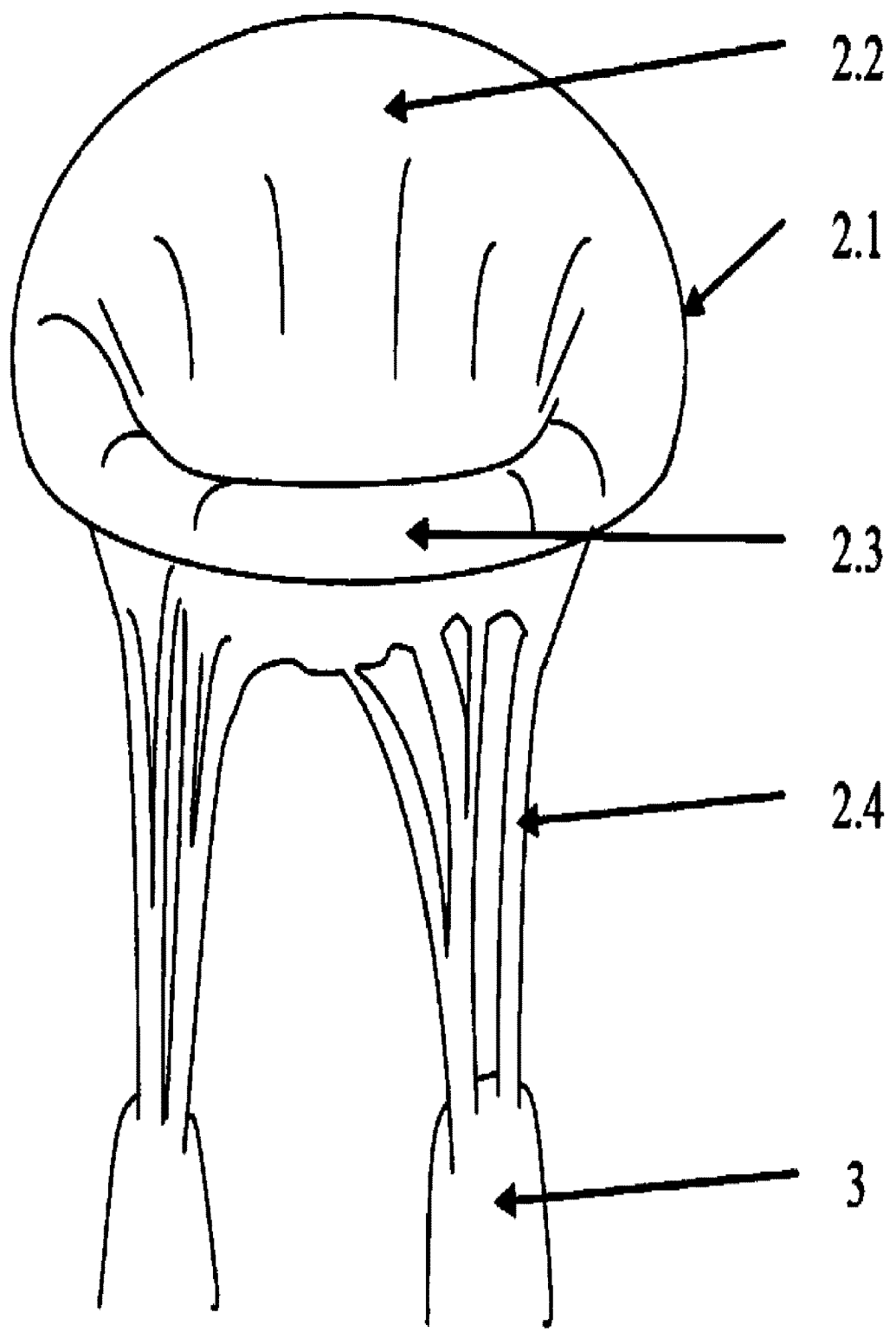
FIG. 2 is a depiction of the mitral valve apparatus.
Figure 3:
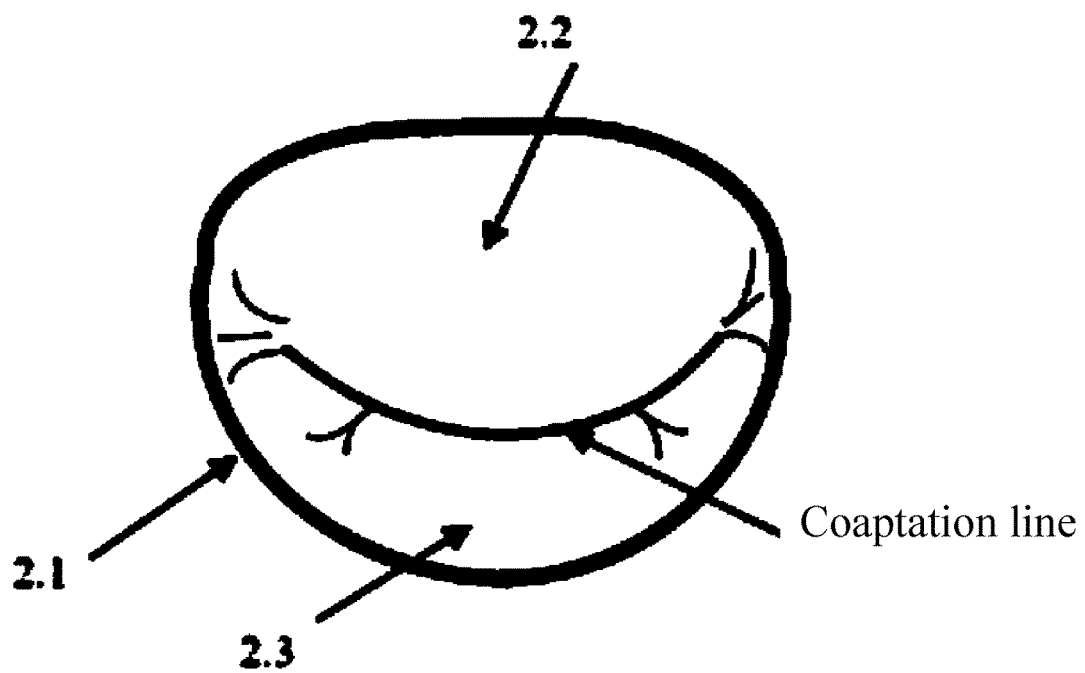
FIG. 3 is a depiction of the lateral view of the mitral valve in the closed position.
Figure 4:
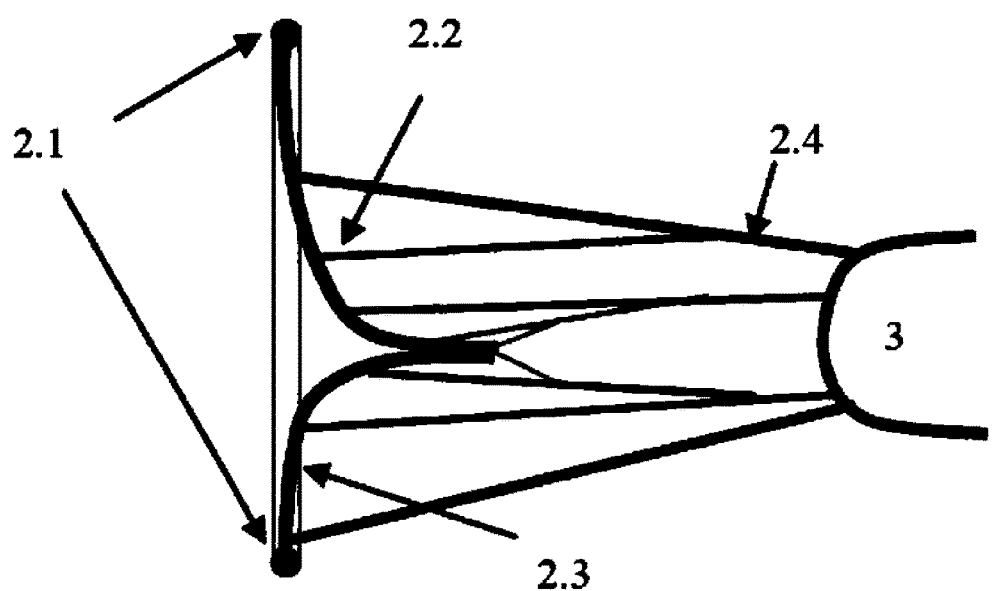
FIG. 4 is a depiction of the atrial view of the mitral valve in the closed position.
Figure 5:
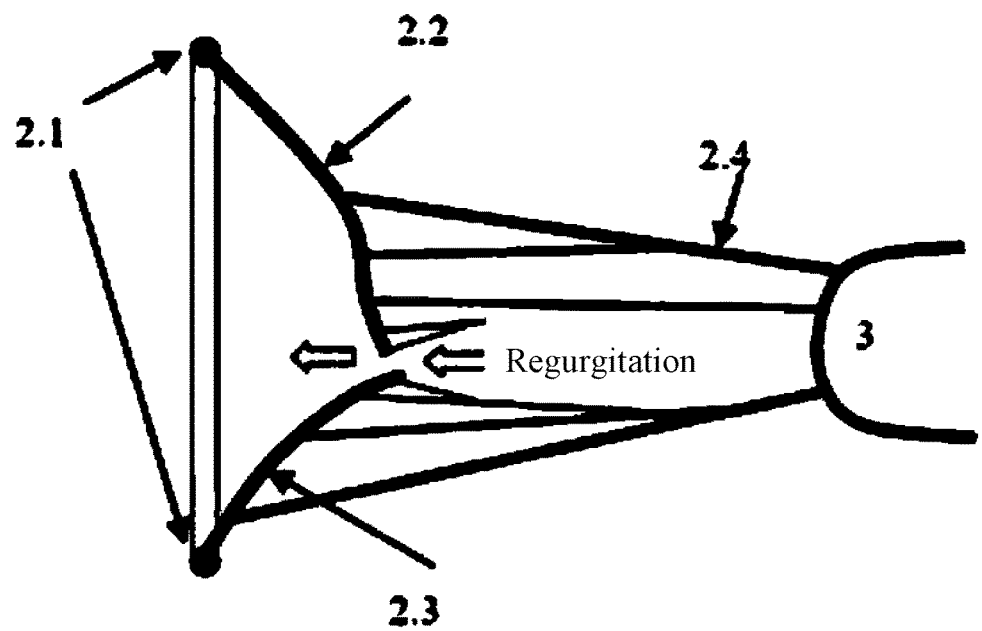
FIG. 5 is a depiction of the lateral view of mitral valve in the closed position showing miscoaptation and leakage during systole.
Figure 6:
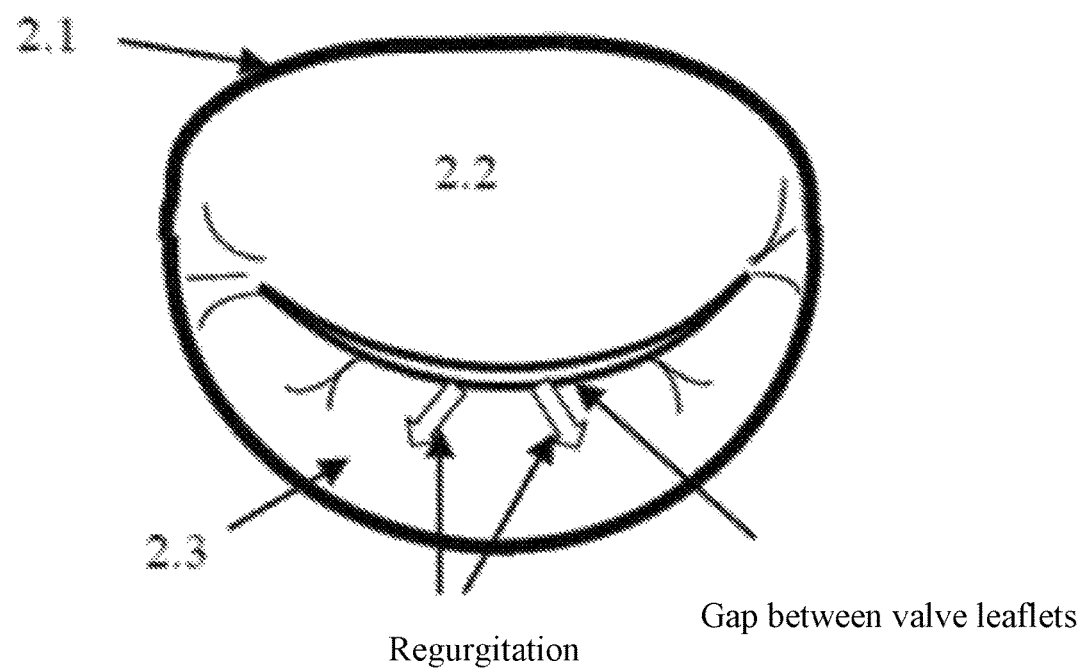
FIG. 6 is a depiction of the of the atrial view of the mitral valve in the closed position showing miscoaptation and leakage during systole.
Figure 7:
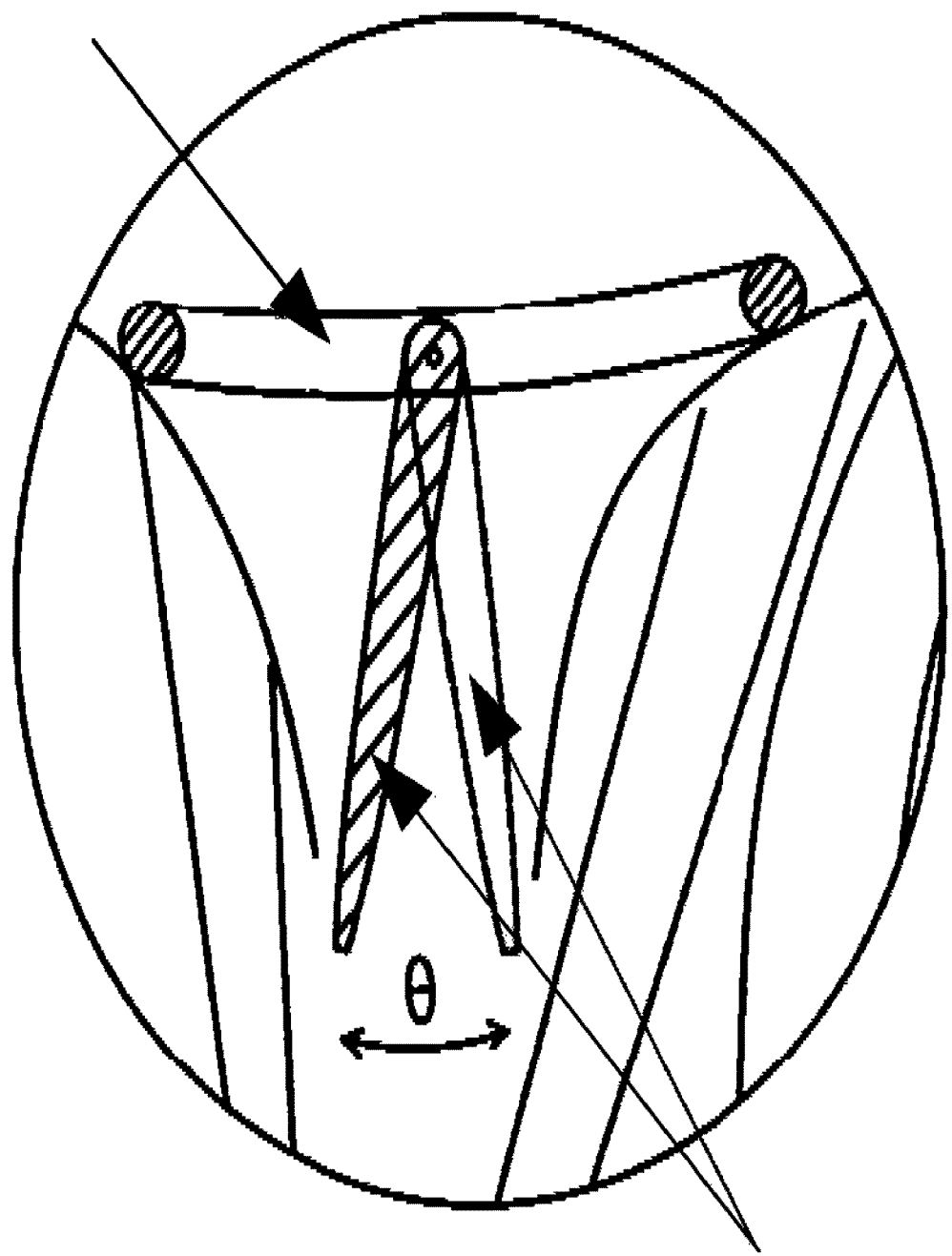
FIG. 7 is a swing depiction of the valve coaptation plate occluder of self-adjustable positioning mitral.
Figure 8:
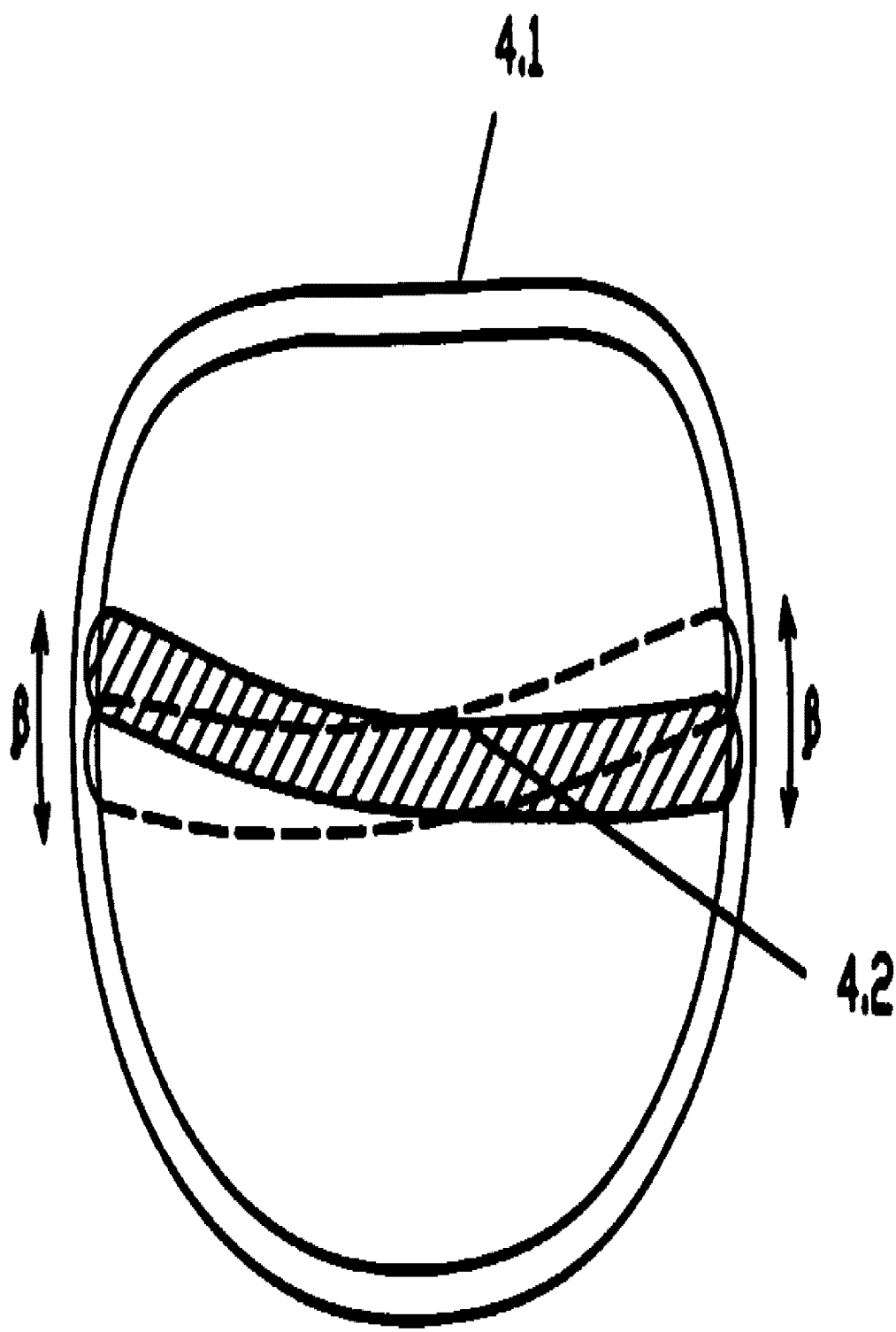
FIG. 8 is a rolling depiction of the mitral valve coaptation plate occluder of self-adjustable positioning.

All figures referred to will use the following descriptions for reference numbers: left atrium (1), mitral valve (2), annulus (2.1), anterior leaflet (2.2), posterior leaflet (2.3), chordate (2.4), papillary muscle (3), suture ring (4.1), coaptation plate (4.2), extension rods or bar (4.3), left ventricle (5).

DETAILED DESCRIPTION

Illustration of this invention will be further clarified by the attached figures and specific implementation, but the protection scope of the invention is not limited to them.

The invention provides a device of the mitral valve coaptation plate occluder of self-adjustable positioning for repairing mitral regurgitation, including the annuloplasty ring 4.1 sutured on the mitral annulus 2.1 and coaptation plate 4.2. The coaptation plate 4.2 comprises a tongue plate and a supporting rod 4.3 at the top of the tongue plate connecting the annuloplasty ring. The coaptation plate 4.2 connecting on the annuloplasty ring 4.1 can swing and roll.

The coaptation plate (4.2) is made of rigid or flexible materials. If rigid materials, the tongue plate (4.2) matches the free edges of the leaflets (2.2 and 2.3) during mitral valve closure. If flexible materials, the flexible tongue plate has no arc, and it can swing and roll under the pressure of the anterior and posterior leaflets and touch the free edge of the mitral leaflets. The connecting mode of the coaptation plate and annuloplasty ring has many ways, and the hinge or fixed connection can be chosen under the guarantee of the coaptation plate have the ability of swinging and rolling. For the hinge connection, the coaptation plate has the ability of swinging and rolling by the hinge to realize self-adjustable positioning. Thus, the tongue plate can be made by rigid or flexible materials. For the fixed connection, the flexible coaptation plate has the ability of swinging and rolling by its own flexibility to realize self-adjustable positioning. The annuloplasty ring can be sutured on the patient's mitral annulus by the open heart surgery. The annuloplasty ring plays a role of correcting the dilated mitral annulus and supporting the coaptation plate. When the heart valve is closed, the coaptation plate will swing or roll according to the regurgitation gap location of the free edges of the mitral leaflets to realize self-adjustable positioning. The coaptation plate blocks the regurgitation gap and touch the free edge of the mitral leaflets to reduce or prevent regurgitation during systole.

Preferably, the coaptation plate 4.2, the support rod 4.3 and the outer surface of the suture ring 4.1 are wrapped with a layer of blood compatible material, such as polyurethane or pericardial membrane in order to improve the compatibility of the coaptation plate 4.2 and blood. A layer of fabric material is wrapped around the outer surface of the annuloplasty ring 4.1, which is convenient to sew the annuloplasty ring 4.1 on the mitral annulus 2.1.

EXAMPLE 1

Figure 9:
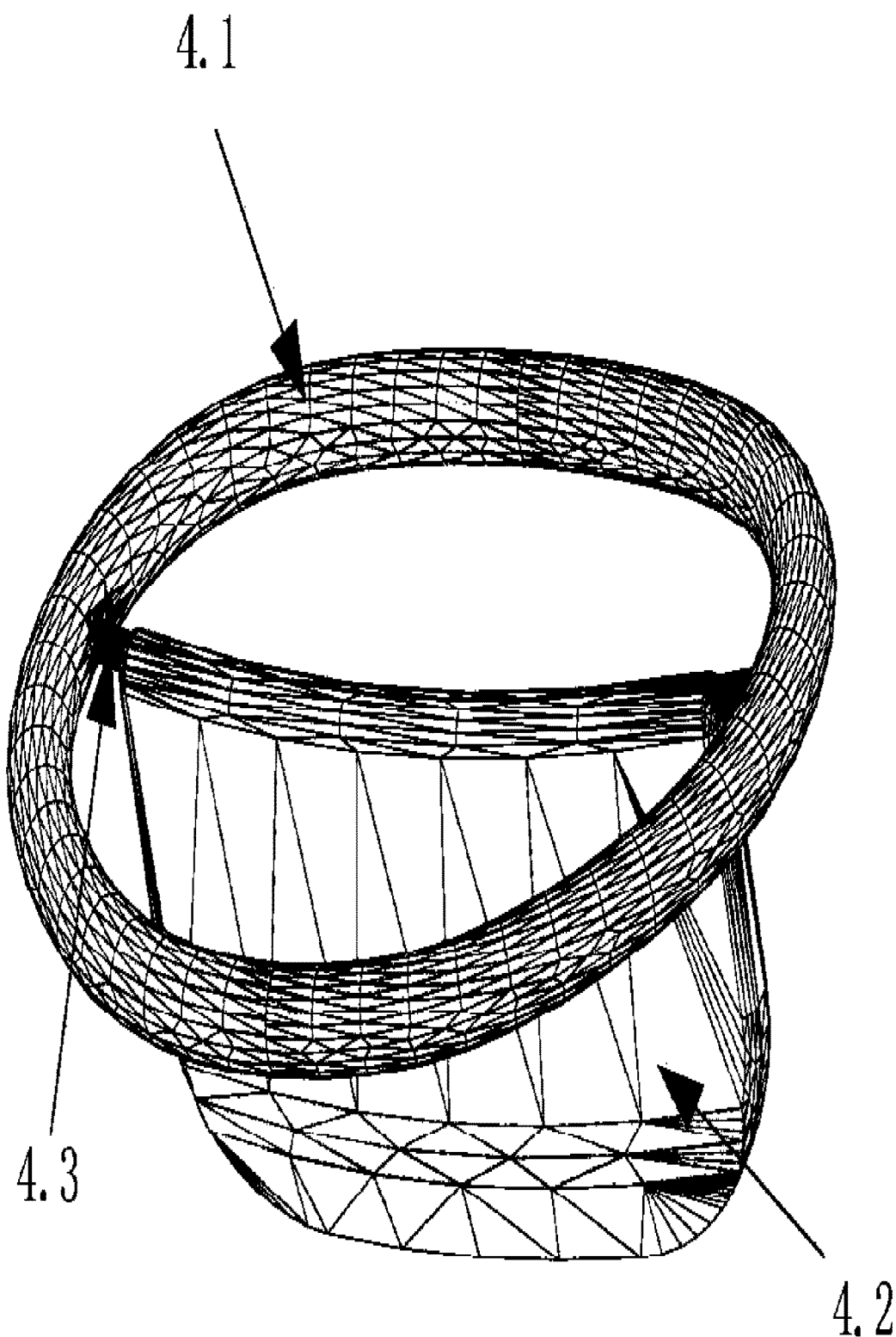
FIG. 9 is a 3D view of the mitral valve coaptation plate occluder of self-adjustable positioning in the first example.
Figure 10:
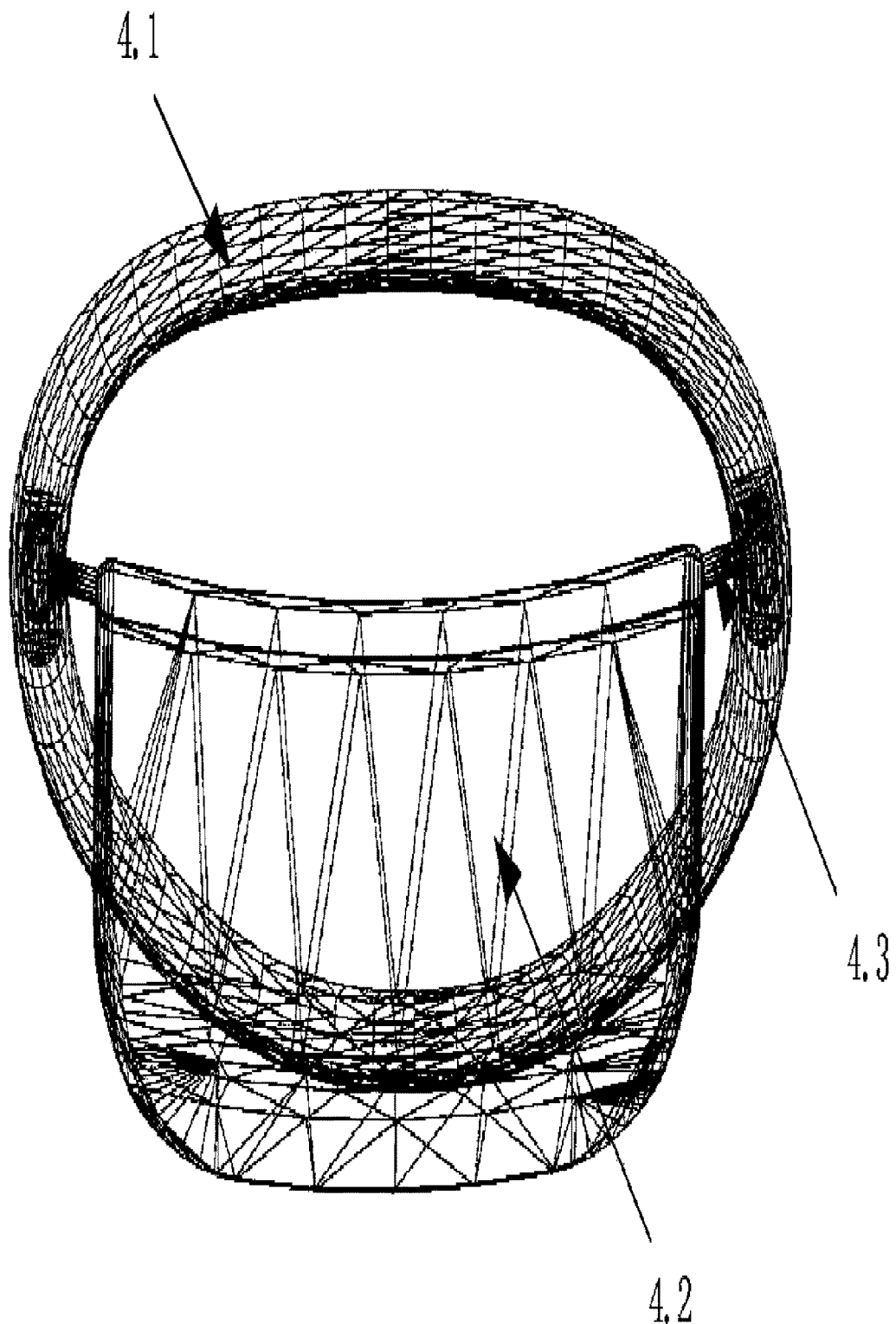
FIG. 10 is a depiction of a sectional view in the circumferencial direction of annuloplasty ring of the mitral valve coaptation plate occluder of self-adjustable positioning in the first example.
Figure 11:
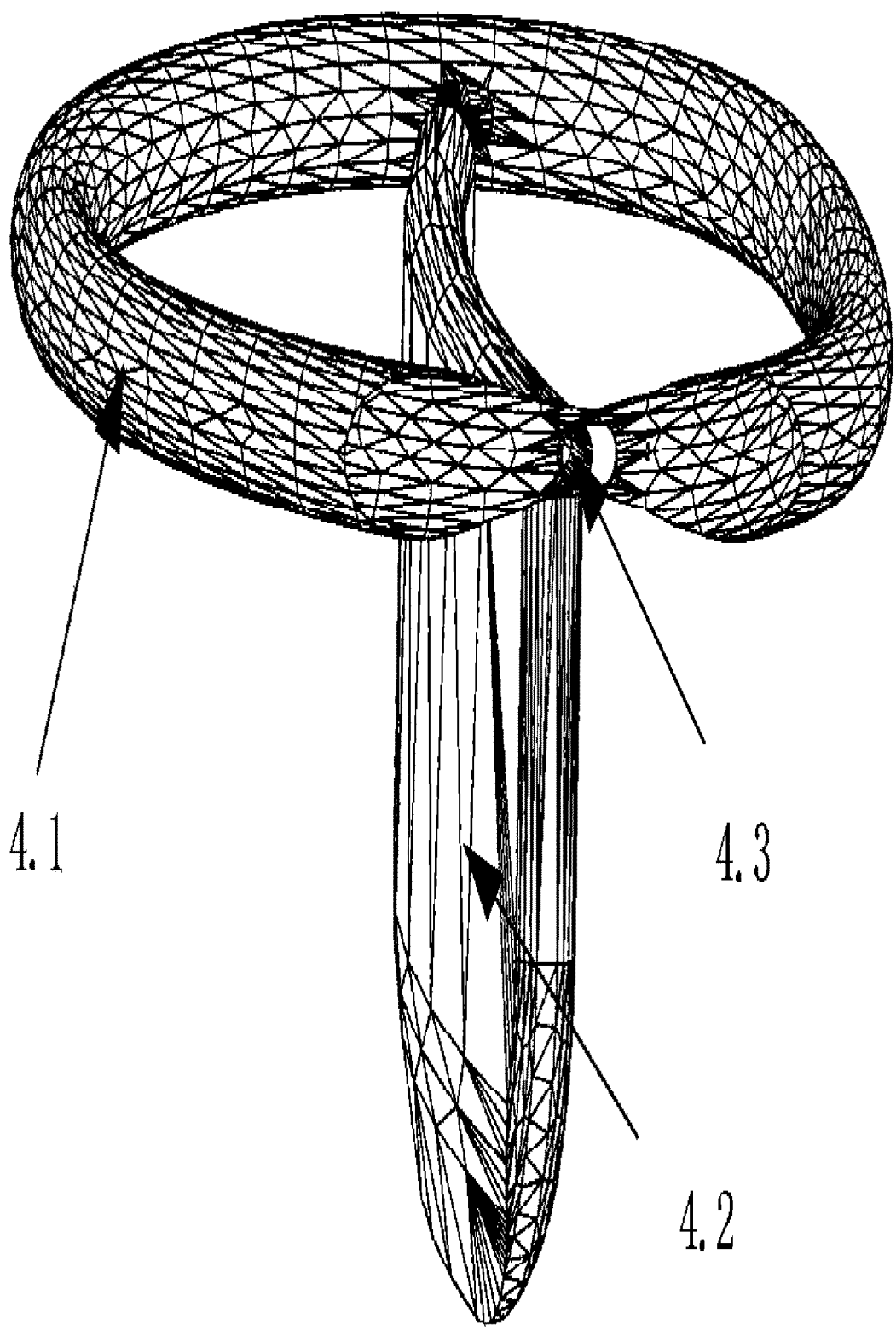
FIG. 11 is a depiction of a partial sectional view of the annuloplasty ring of the mitral valve coaptation plate occluder of self-adjustable positioning in the first example.

FIG. 9, FIG. 10, FIG. 11 is the first invention example of mitral valve coaptation plate occluder of self-adjustable positioning. In this embodiment, the coaptation plate 4.2 is made of a rigid material. The tongue plate 2 must have the same arc with the coaptation line of the free edges of the anterior and posterior leaflets of the mitral valve. The tongue plate and supporting rod are one part. The two curved cylinders are located at the both ends of the supporting rod, and they are perpendicular to the supporting rod. The cylinder and the annuloplasty ring have the same arc. There are two cylindrical cavities and the oblong hole in the plastic ring suture. The cylindrical cavities are parallel with the suture ring at the connection position of the supporting rod. The oblong hole connected cylindrical cavity and external. The diameter and length of the cylindrical cavity are larger than the cylinder. The supporting rod is inserted into the oblong hole. The two ends of the supporting rod 4.3 are inserted into the cylindrical cavities. The cylinder can produce small transposition distance in the cylindrical cavity to achieve a small angle of swinging. The cylinder can produce small transposition distance along the suture ring circumferential direction in the cavity to achieve the rolling of the coaptation plate. In summary, the coaptation plate can achieve adaptive positioning by the way of its swinging and rolling.

EXAMPLE 2

Figure 12:
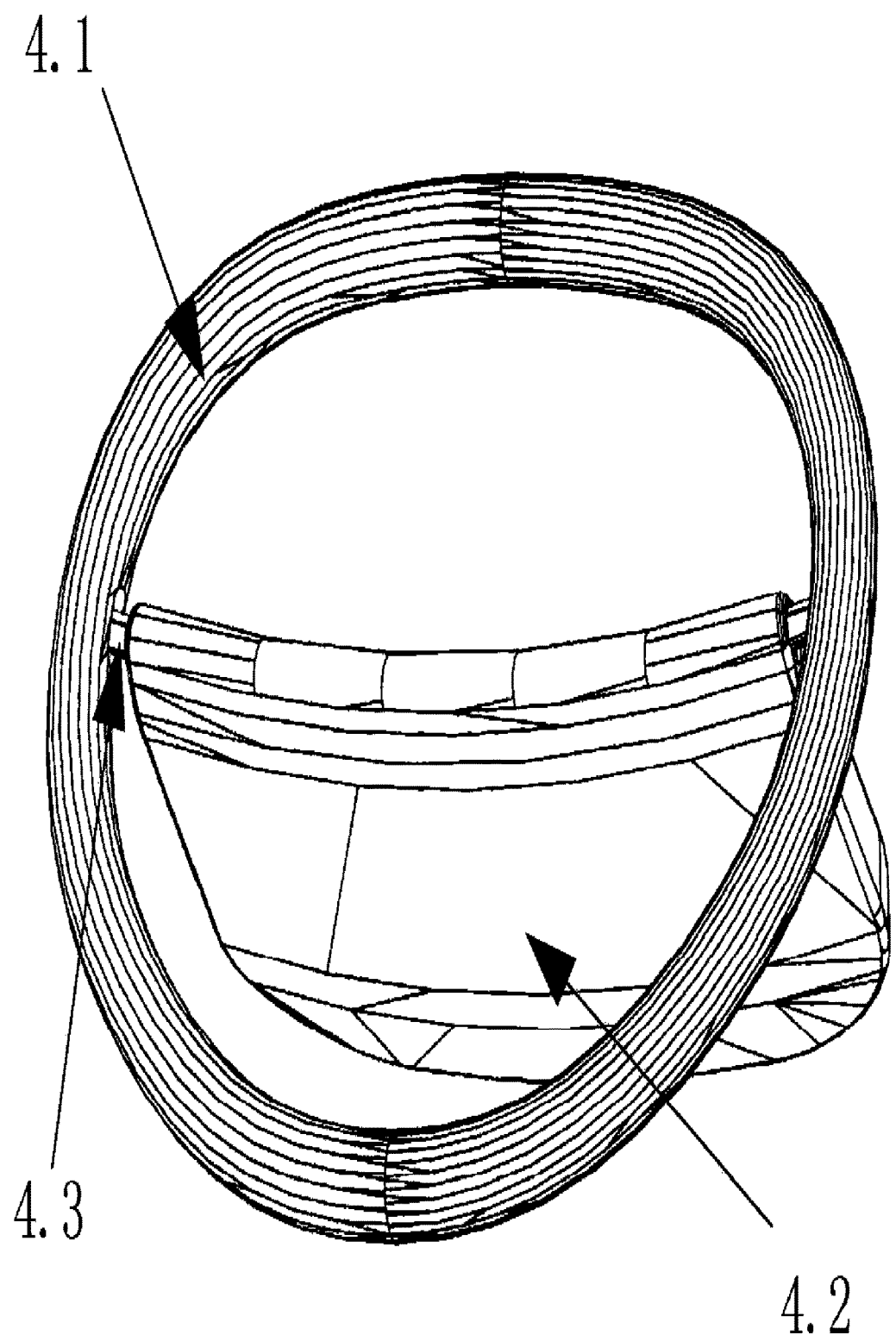
FIG. 12 is a 3D view of the mitral valve coaptation plate occluder of self-adjustable positioning in the second example.
Figure 13:
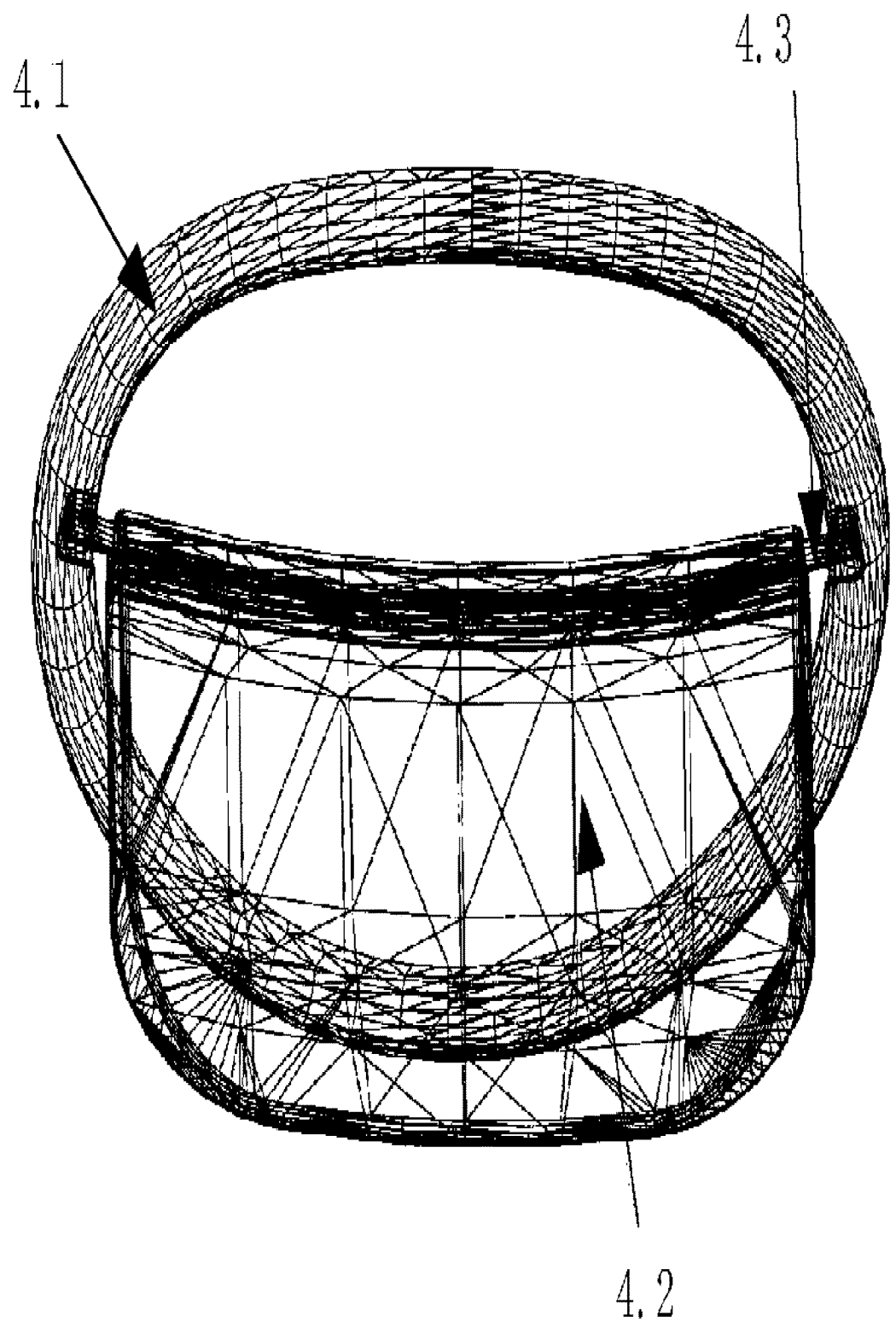
FIG. 13 a depiction of a sectional view in the circumferential direction of the annuloplasty ring of the mitral valve coaptation plate occluder of self-adjustable positioning in the second example.
Figure 14:
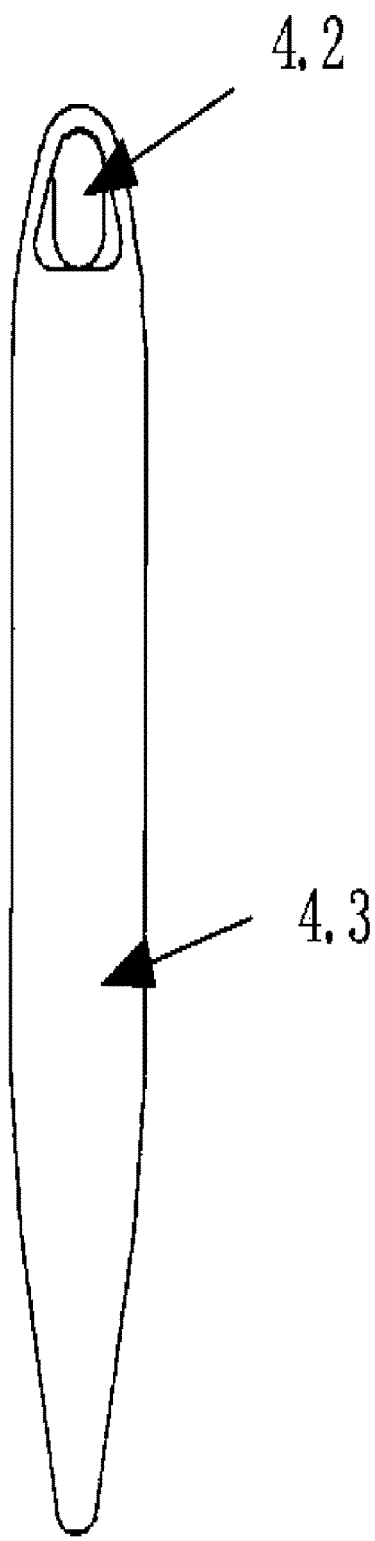
FIG. 14 is a depiction of a sectional view of the annuloplasty ring of the mitral valve coaptation plate occluder of self-adjustable positioning in the second example.

As shown in FIG. 12, FIG. 13, FIG. 14, the coaptation plate is made of a rigid material. The tongue plate must have the same arc with the coaptation line of the free edges by the anterior and posterior leaflets of the mitral valve. There are triangular holes at the top of the tongue plate. Three vertices of the triangular-like holes are rounded. The support rod is inserted into a triangular hole. The contact part of the support rod 4.3 and the tongue plate is oblong, and its transverse length is less than the longitudinal length in the cross section. The two ends of the support rod 4.3 are cylindrical, the annuloplasty ring 4.1 has two oblong holes, and its transverse length is greater than the longitudinal length. The two ends of the supporting rod 4.3 are inserted into the oblong holes. Triangular holes are matched with the oblong support rod 4.3, while small clearance in the upper part and big clearance in the lower part, by which means to achieve a small angle of swinging. The two ends of the supporting rod can produce small transposition distance in oblong hole along the circumferential direction to achieve rolling the of the coaptation plate. In summary, the coaptation plate can achieve adaptive positioning by the way of its swinging and rolling.

EXAMPLE 3

Figure 15:
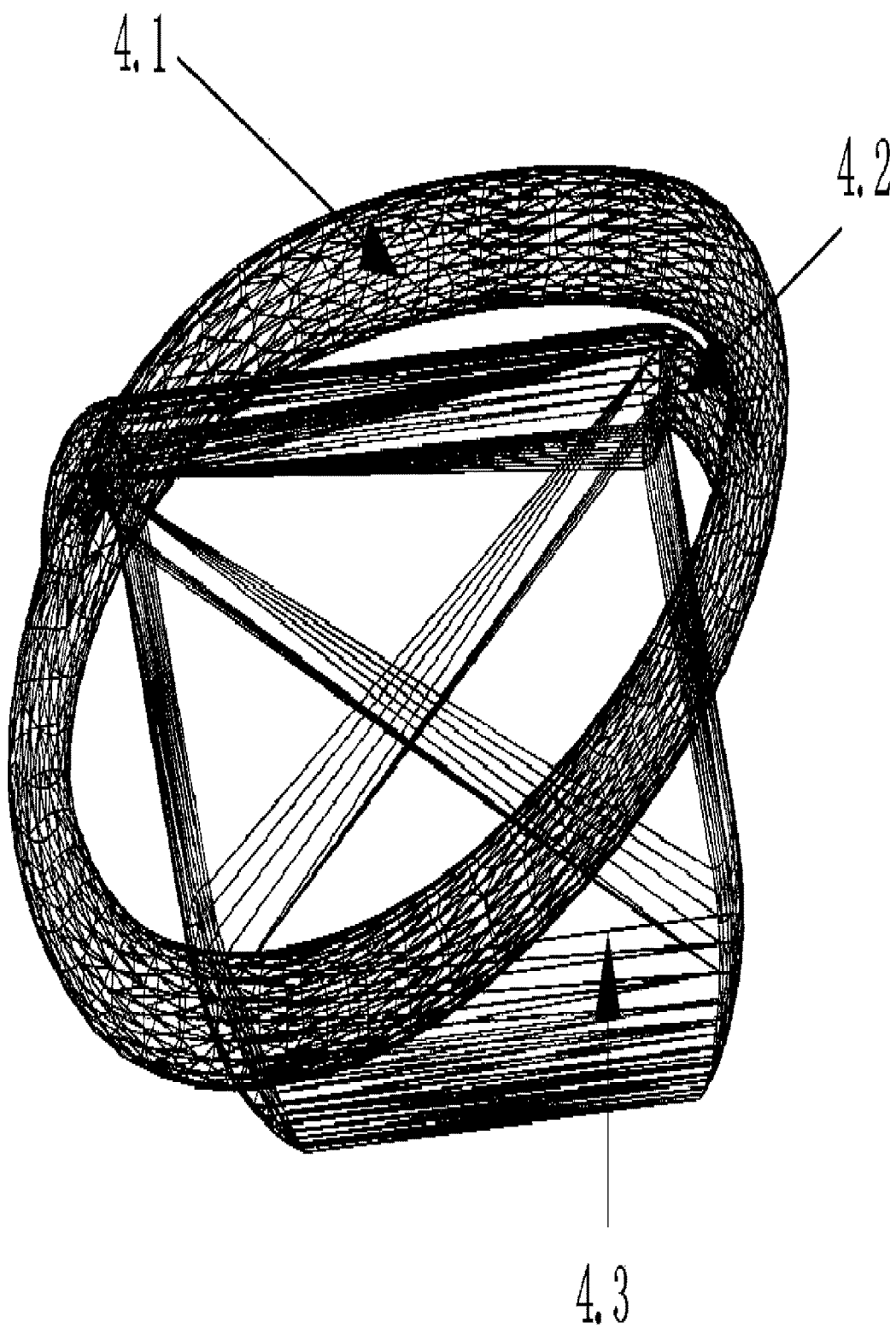
FIG. 15 is a depiction of a sectional view of the annuloplasty ring of the mitral valve coaptation plate occluder of self-adjustable positioning in the third example.

As shown in FIG. 15, the tongue plate 4.2 is made of a flexible material, and the supporting rod 4.3 is fixedly connected with the suture ring 4.1. The tongue plate can swing and roll by means of its own flexibility, and the coaptation plate 4.2 finally realizes adaptive positioning. The flexible tongue plate has embedded by elastic metal or polymer materials frame. The framework is used to keep the flexible tongue plate shape from large deformation and warping under the pressure caused by the anterior and posterior leaflets. However, the flexibility of framework must satisfy requirements of the elastic deformation caused by the pressure of the anterior and posterior leaflets and make the flexible tongue plate swing and roll, as well as deform into a curved shape. Preferably, the height of the supporting rod is above than the plane of the suture ring, in other words, the connection of the closed plate and the annuloplasty ring is raised to the side of the atrium to reduce the swing angle in order to ease the damage caused by the hinge fatigue The implementation methods is the preferred embodiment of the present invention, however the invention is not limited to this mentioned above. Without departing from the substance of the present invention, any obvious improvement, replacement or modification made by the technical staff in the field all belong to the protection scope of the invention.

We claim:

1. A mitral valve coaptation plate occluder of self-adjustable positioning for repairing mitral regurgitation comprising:
    an annuloplasty ring sutured on a mitral annulus and a coaptation plate wherein the annuloplasty ring and coaptation plate comprise a rigid material;
    the coaptation plate wrapped with a layer of blood compatible material comprising a tongue plate and a supporting rod at a top of the tongue plate connecting the annuloplasty ring wherein the tongue plate comprises the same arc of coaptation line with the closed free edges of the anterior and posterior leaflets;
    a hinge connection provided between the supporting rod and the annuloplasty ring, wherein the tongue plate and the supporting rod operate as a single part;
    two curving cylinders located at both ends of the supporting rod, wherein the cylinders are perpendicular to the supporting rod, where the cylinders and the annuloplasty ring having the same arc; and
    two cylindrical cavities and an oblong hole in the annuloplasty ring wherein the cylindrical cavities are parallel with the annuloplasty ring at the connecting position of the supporting rod and the oblong hole connects to the external cylindrical cavity;
    wherein the diameter and length of the cylindrical cavity are larger than the cylinders;
    wherein the supporting rod is inserted into the oblong hole and the two ends of the supporting rod are inserted into the cylindrical cavity; and
    wherein the coaptation plate connecting on the annuloplasty ring can swing and roll.

2. The apparatus of claim 1, wherein the support rod and an outer surface of the annuloplasty ring are wrapped with fabric materials.

3. The apparatus of claim 1, wherein the blood compatible material is at least one of a polyurethane or a pericardial membrane.

4. The apparatus of claim 1, wherein there is a rigid connection between the supporting rod and annuloplasty ring.

* * * * *